United States Patent [19]

Carnahan

[11] Patent Number: 6,080,845
[45] Date of Patent: Jun. 27, 2000

[54] MONOCLONAL ANTIBODY AGAINST UTRICULAR EPITHELIUM

[75] Inventor: Josette F. Carnahan, Newbury Park, Calif.

[73] Assignee: Amgen Inc., Thousands Oaks, Calif.

[21] Appl. No.: 09/238,182

[22] Filed: Jan. 28, 1999

Related U.S. Application Data

[63] Continuation-in-part of application No. 09/129,549, Aug. 5, 1998, abandoned.

[51] Int. Cl.$^7$ ..................................................... C12P 21/08
[52] U.S. Cl. ................................... 530/388.24; 530/388.1
[58] Field of Search .......................... 530/387.1, 387.7, 530/388.1, 388.23, 388.24, 388.85; 435/325, 326, 335, 336, 366.1

[56] References Cited

U.S. PATENT DOCUMENTS

| | | |
|---|---|---|
| 5,665,862 | 9/1997 | Fischbach et al. . |
| 5,670,342 | 9/1997 | Carnahan et al. . |
| 5,686,415 | 11/1997 | Carnahan et al. . |
| 5,763,213 | 6/1998 | Ho et al. . |

FOREIGN PATENT DOCUMENTS

| | | |
|---|---|---|
| WO 94/28133 | 12/1984 | WIPO . |
| WO 92/20798 | 11/1992 | WIPO . |

OTHER PUBLICATIONS

Campbell, Monoclonal Antibody Technology, Elsevier Science publishers, Chapter 1, 1986.
Valat et al, J. Neurocytology vol. 24 p. 916, 1995.
Zheng et al, J. neurosicence vol. 17 p. 216, Jan. 1997.
Kuijpers et al, Histochemistry vol. 96 p. 511, 1991.
Crouch et al, J. Histochemistry and Cytochemistry vol. 45 p. 773, Jun. 1997.
Peles et al., Cell, vol. 69, pp. 205–216 (1992).
Wen et al., Cell, vol. 69, pp. 559–572 (1992).
Holmes et al., Science, vol. 256, pp. 1205–1210 (1992).
Bacus et al., Cancer Research. vol. 53, pp. 5251–5261 (1993).
Plowman, Nature, vol. 366, pp. 473–475 (1993).
Kita et al., FEBS Letters, vol. 349, pp. 139–143 (1994).
Carraway et al., Journal of Biological Chemistry, vol. 269, No. 19, pp. 14303–14306 (1994).
Falls et al., Cell, vol. 72, pp. 801–805 (1993).
Marchionni et al., Nature, vol. 362, pp. 312–316 (1993).
Wen et al., Molecular and Cellular Biology, vol. 14, No. 3, pp. 1909–1919 (1994).
Kita et al., Biochemical and Biophysical Communications, vol. 210, No. 2, pp. 441–451 (1995).

*Primary Examiner*—Sheela Huff
*Attorney, Agent, or Firm*—Richard J. Mazza; Ron K. Levy; Steven M. Odre

[57] ABSTRACT

A non-naturally occurring peptide derived from EGF-like domains of NDF/heregulin protein isoforms is used to stimulate the proliferation of cells in the sensory epithelium of the inner ear. A monoclonal antibody against adult rat utricular epithelium is also described.

1 Claim, 5 Drawing Sheets

Fig. 1

SHLVKCAEKEKTFCVNGGECFMVKDLSNPSRYLCK
CQPGFTGARCQNYVMAS

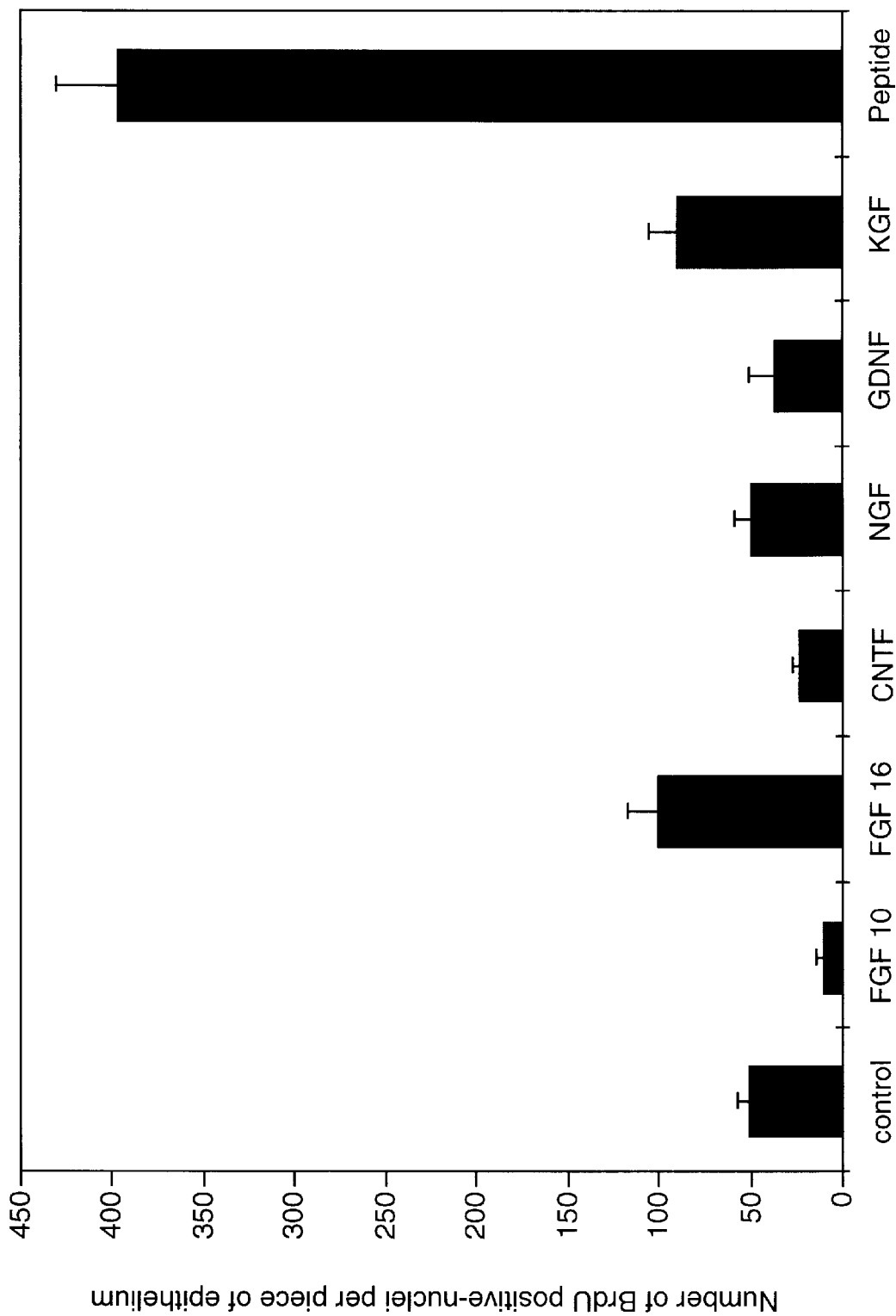

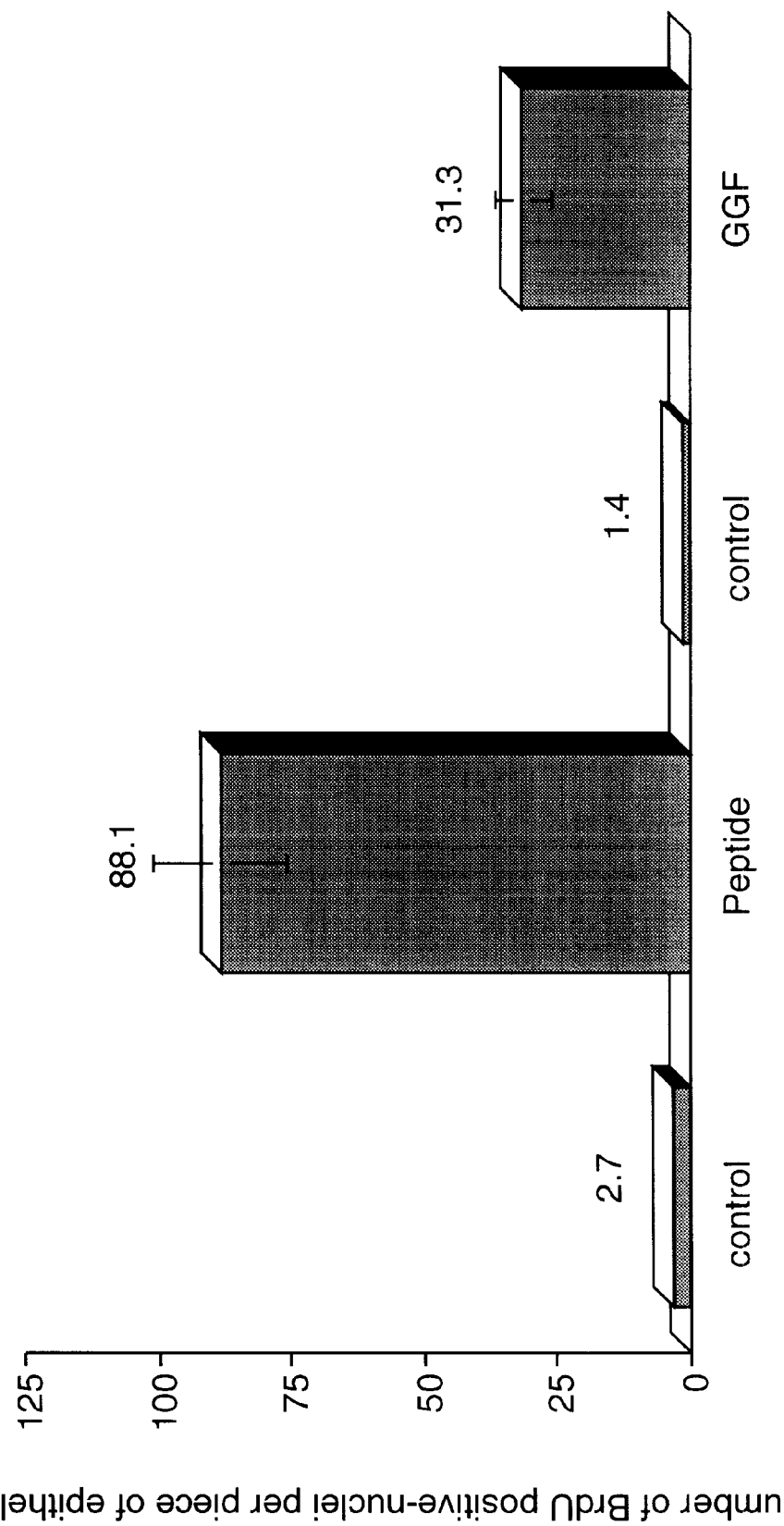

NDF

Control

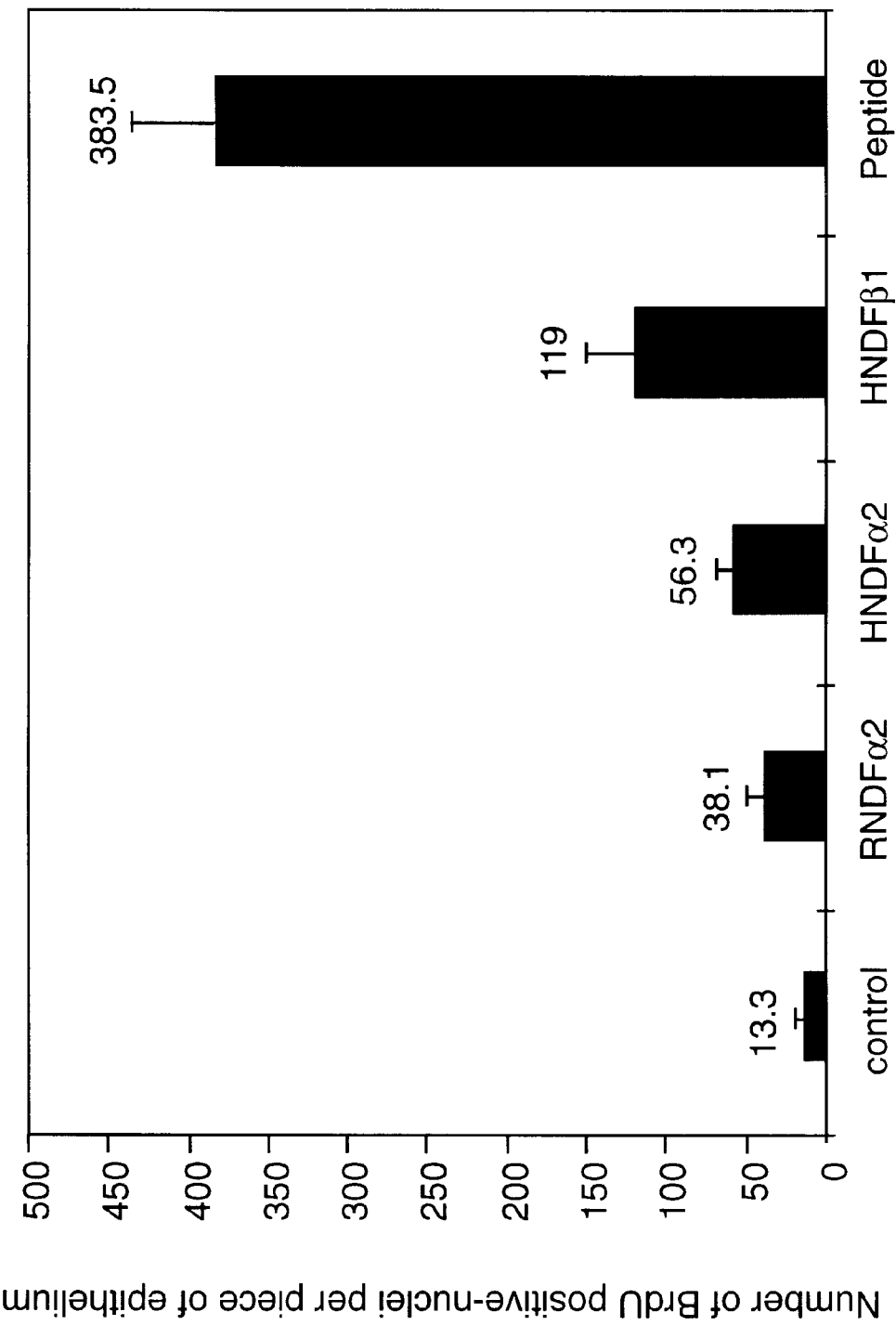

MONOCLONAL ANTIBODY AGAINST UTRICULAR EPITHELIUM

CROSS-REFERENCE TO RELATED APPLICATION

This application is a continuation-in-part of application Ser. No. 09/129,549, filed Aug. 5, 1998, now abandoned the entire disclosure of which is incorporated herein by reference.

FIELD OF THE INVENTION

This invention relates to the NDF/heregulin protein family, and more specifically to the use of a derivative peptide to stimulate the proliferation of sensory epithelial cells of the inner ear for the treatment of vestibular disorders. The invention also relates to monoclonal antibodies raised against adult rat utricular epithelium.

BACKGROUND OF THE INVENTION

The NDF/heregulins are a known family of molecules which stimulate the tyrosine phosphorylation of the erbB2/Her2 protooncogene product p185; see Peles et al., Cell, Volume 69, pages 1–14 (1992); Wen et al., Cell, Volume 69, pages 559–572 (1992); Holmes et al., Science, Volume 256, pages 1205–1210 (1992); and Bacus et al., Cancer Research, Volume 53, pages 5251–5261 (1993). Thought at first to be ligands for erbB2/Her2, the NDF/heregulins are now known to bind to and stimulate the kinase activity of erbB3/Her3 and erbB4/Her4; see Plowman et al., Nature, Volume 366, pages 473–475 (1993); Kita et al., FEBS Letters, Volume 349, pages 139–143 (1994); and Carraway et al., Journal of Biological Chemistry, Volume 269, pages 14303–14306 (1994). The NDF/heregulin family is considered to also include ARIA and glial growth factor (GGF); see, respectively, Falls et al., Cell, Volume 72, pages 801–805 (1993), and Marchionni et al., Nature, Volume 362, pages 312–316 (1993).

The NDF/heregulins are transmembrane glycoproteins which, in the main, possess an EGF-like domain in the extracellular portion that may function as a receptor recognition site; Wen et al., Cell, above. The original group of NDF/heregulins comprise at least ten isoforms, which can be divided into two groups, called alpha ($\alpha$) and beta ($\beta$), based on differences in the EGF-like domain. Analysis suggests that the various isoforms are generated by alternative gene splicing and perform distinct tissue-specific functions in vivo; Wen et al., Molecular and Cellular Biology, Volume 14, Number 3, pages 1909–1919 (1994).

Several functions of the NDF/heregulins have been identified, including the induction of either mitogenesis or differentiation in mammary cells (Peles et al., Cell, above); the stimulation of muscle acetylcholine receptors (Falls et al., above); and the mitogenesis of Schwann cells (Marchionni et al., above).

Kita et al. in Biochemical and Biophysical Research Communications, Volume 210, Number 2, pages 441–451 (1995), describe a biologically active 52-amino acid peptide which is based on the sequence of the EGF-like domain of NDF-$\alpha$2 and is produced by chemical synthesis. The peptide is shown to stimulate tyrosine phosphorylation of Her2, Her3 and Her4, and to induce morphological changes in breast cancer cells.

U.S. Pat. No. 5,670,342 (issued Sep. 23, 1997) describes chemically synthesized peptides which are derived from the sequence of the EGF-like domain of NDF and are active in promoting the growth of both Schwann cells and colon epithelial cells. One of these peptides is a "hybrid" ($\alpha/\beta$) molecule composed of sequence from the EGF-like domains of both the alpha($\alpha$) and the beta($\beta$) forms of NDF. See, also, U.S. Pat. No. 5,686,415 (issued Nov. 11, 1997), as well as pending applications Ser. No. 08/761,038 and Ser. No. 08/761,762, both filed Dec. 5, 1996.

SUMMARY OF THE INVENTION

The present invention comprises the use of a peptide of following sequence as a growth stimulant for sensory epithelial cells of the inner ear:
SHLVKCAEKEKTFCVNGGECFMVKDL-SNPSRYLCKCQPGFTGARCQNYVMAS
(SEQ ID NO: 1)

This peptide has been described previously in U.S. Pat. No. 5,670,342 and U.S. Pat. No. 5,686,415 as a hybrid form derived from the EGF-like domains of NDF-$\alpha$ and NDF-$\beta$. However, the usefulness of this molecule as a growth stimulant for sensory epithelial cells of the utricle in the inner ear, which is demonstrated in the working examples below, has not been previously recognized. Because all of the vestibular organs (e.g., utricle, semicircular canal, etc.) have similar cellular organization, it is reasonable to assume that they will respond in the same way to contact and treatment with the present peptide. Thus, the peptide is expected to be useful to treat vestibular disorders such as, for example, loss of balance due to utricular degeneration or disease in mammals, including humans. The peptide may also be useful to treat hearing loss in mammals, including humans, which is attributable to the degeneration of inner ear hair cells, i.e., by regenerating such hair cells in association with sensory epithelium.

An additional aspect of the invention comprises monoclonal antibodies raised against adult rat utricular epithelium, which are especially useful in study and research with such organs and tissue, e.g., because of their applicability for differential staining.

BRIEF DESCRIPTION OF THE FIGURES

FIG. 1. This figure depicts the primary structure (amino acid sequence) of the peptide used in the method of this invention (SEQ ID NO: 1).

FIG. 2. This figure is a graph comparing (in cell culture) the mitogenic activity (as BrdU-positive cell nuclei) of the peptide of SEQ ID NO: 1 (designated as "Peptide") with other growth factors (FGF-10, FGF-16, CNTF, NGF, GDNF and KGF) on the utricular epithelium from seven day-old rats.

FIG. 3. This figure is a graph comparing (in cell culture) the mitogenic activity of the peptide of SEQ ID NO: 1 ("Peptide") with glial growth factor (GGF) on adult rat utricular epithelium. As in FIG. 2, bromo-2'deoxy-uridine (BrdU) incorporation was used as a measure of the mitogenic activity, with an anti-BrdU antibody being used for the immunostaining of BrdU-positive cell nuclei.

FIG. 5. This figure is a graph comparing the mitogenic activity (as BrdU-positive nuclei) of the peptide of SEQ ID NO: 1 ("Peptide") with other NDF/heregulin-derived peptides on inner ear sensory epithelial cells.

DETAILED DESCRIPTION OF THE INVENTION

Figure 4A:
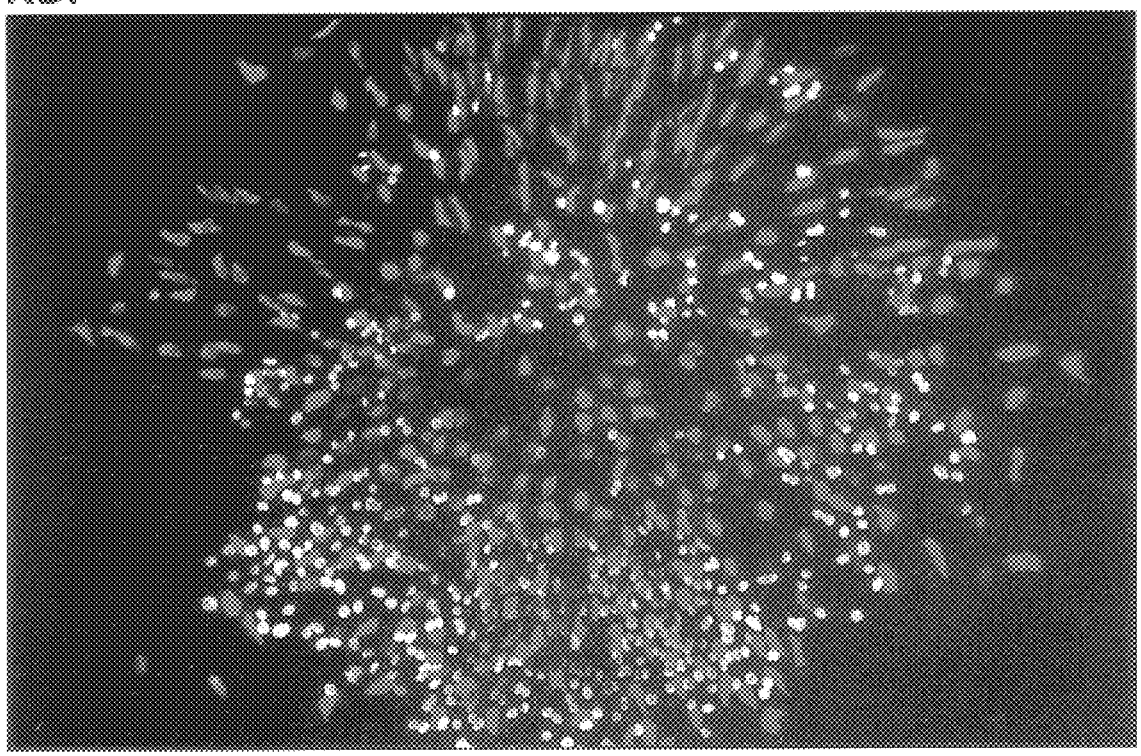
FIG. 4A–4B. This figure illustrates the increase in Bromo-2'deoxy-uridine (BrdU) incorporation, induced by the peptide of SEQ ID NO: 1, as a measure of mitogenic activity in supporting cells of an epithelial cell culture. The cells were derived from the utricle of a one week-old rat. The presence of BrdU in the form of BrdU-positive cell nuclei is represented by the lighter dots. Immunostaining with calretinin (grayish spots) shows the presence of hair cells.

The present invention contemplates the use of isolated peptide having the primary structural conformation (i.e., continuous sequence of amino acid residues) of SEQ ID NO: 1 (see also FIG. 1). The term "purified and isolated" herein means substantially free of unwanted substances so that the peptide is useful the described intended purpose, i.e., as an agent for causing the proliferation of vestibular sensory epithelial cells and growth of vestibular sensory epithelium.

The usefulness of the peptide of SEQ ID NO: 1 as a mitogenic agent for vestibular sensory epithelial cells lends itself to the therapeutic treatment of balance disorders, such as vertigo or other chronic or acute types of dysequilibrium or dizziness attributable to vestibular organ degeneration and malfunction.

The mitogenic activity of the peptide of SEQ ID NO: 1 on the vestibular sensory epithelium of the mammalian inner ear suggests that it may also be useful to regenerate hair cells, which are critical for hearing. Thus, the peptide may be beneficial for treating hearing loss associated with deteriorated or damaged inner ear hair cells, and such applications are included within the therapeutic treatments made possible by the present invention.

The peptide of SEQ ID NO: 1 can be prepared by the use of chemical synthesis procedures. Alternatively, the peptide can be the product of recombinant expression of exogenous cDNA (obtained by DNA synthesis), the nucleic acid molecule of SEQ ID NO: 2, for the example, in a prokaryotic or eukaryotic host (e.g., bacterial, yeast, higher plant, insect or mammalian cells in culture).

Suitable methods of chemical synthesis are well known to the skilled artisan; see Engels et al., Angew. Chem. Intl. Ed., Volume 28, pages 716–734 (1989). Such methods include the phosphotriester, phosphoramidite and H-phosphonate methods for nucleic acid synthesis. A preferred method involves polymer supported synthesis using standard phosporamidite chemistry.

Merely by way of example, the peptide of SEQ ID NO: 1 can be prepared directly from the method of fluorenylmethoxycarbonyl/t-butyl-based solid phase chemistry method described in U.S. Pat. No. 5,670,342, followed by folding into active product in a buffered solution composed of TRIS, EDTA and glutathione, and purification.

If recombinant methods of production for the peptide are used, the product such of expression in typical yeast (e.g., *Saccharomyces cerevisiae*), insect, or prokaryote (e.g., *E. coli*) host cells will, like chemical synthesis, also be free of association with any mammalian proteins. The product of expression in vertebrate (e.g., non-human mammalian such as COS or CHO, and avian) cells is typically free of association with any human proteins. The peptide may also include an initial methionine amino acid residue (at position –1 with respect to the first amino acid residue of the mature peptide).

Variant nucleic acid molecules having sequences which differ from SEQ ID NO: 2 but still encode the peptide of SEQ ID NO: 1 may be produced. Such variants would also include those containing nucleotide substitutions accounting for codon preference in the host cell being employed for expression.

The nucleic acid molecule of SEQ ID NO: 2, or a variant thereof encoding the peptide of SEQ ID NO: 1, can be inserted into any suitable expression vector using standard ligation techniques. The vector is selected to be functional in the particular host employed (i.e., the vector is compatible with the host cell machinery, such that expression of the nucleic acid encoding the peptide can occur). The peptide may be expressed in prokaryotic, yeast, insect (baculovirus systems) or eukaryotic cells as the host.

The vectors used in any of the host cells to express the peptide may also contain a 5' flanking sequence (also referred to as a "promoter") and other expression regulatory elements operatively linked to the nucleic acid molecule (DNA) to be expressed, as well as enhancer(s), an origin of replication element, a transcriptional termination element, a complete intron sequence containing a donor and acceptor splice site, a signal peptide sequence, a ribosome binding site element, a polylinker region for inserting the nucleic acid encoding the peptide to be expressed, and a selectable marker element, as those skilled in the art will know.

Insertion of the vector into the selected host cell (also referred to as "transformation" or "transfection") may be accomplished using known materials or methods such as calcium chloride, electroporation, microinjection, lipofection, or the DEAE-dextran method.

The host cell, when cultured under suitable nutrient conditions, will synthesize the peptide, which can subsequently be collected by isolation from the culture medium (if the host cell secretes it into the medium) or directly from the host cell (if not secreted). For peptide situated in the host cell cytoplasm and/or nucleus, the host cells are typically first disrupted mechanically or with detergent to release the intracellular contents into a buffered solution. The peptide can then be collected from this solution.

Selection of the host cell will depend in part on whether the host cell is able to "fold" the peptide into its native tertiary structure such that biologically active material is prepared by the cell. Even where the host cell does not synthesize the peptide in the proper conformation, the peptide may be "folded" after synthesis using appropriate chemical conditions.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, and primary explants are also suitable. Candidate cells may be genotypically deficient in the selection gene, or may contain a dominantly acting selection gene. Other suitable mammalian cell lines include, but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells are bacterial cells. For example, the various strains of *E. coli* (e.g., HB101, DH5α, DH10, and MC1061) are well-known as host cells in the field of biotechnology. Various strains of B. subtilis, Pseudomonas spp., other Bacillus spp., Streptomyces spp., and the like may also be employed in this method.

Host cells containing the vector may be cultured using standard media well known to the skilled artisan. The media will usually contain all of the nutrients necessary for the growth and survival of the transformed cells. Suitable media for culturing *E. coli* cells are, for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for the culturing of insect cells is Grace's medium supplemented with yeastolate, lactalbumin hydrolysate and/or fetal calf serum, as necessary.

Typically, an antibiotic or other compound useful for selective growth of the transformed cells is added as a supplement to the growth medium. The compound to be used will be dictated by the selectable marker element present on the plasmid with which the host cell has been transformed or transfected. For example, where the selectable marker element is kanamycin resistance, the compound added to the culture medium will be kanamycin.

Purification of the peptide from solution can be accomplished using a variety of techniques. If the peptide has been synthesized such that it contains a "tag", it may essentially be purified in a one-step process by passing the solution through an affinity column where the column matrix has a high affinity for the tag or for the peptide directly (i.e., a monoclonal antibody specifically recognizing the peptide). Where, on the other hand, the peptide is prepared without a tag attached, and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing. In some cases, it may be preferable to use more than one of these methods for complete purification.

One may modify the peptide of SEQ ID NO: 1 to create a fusion molecule with another peptide sequence. For example, if one desired to "tag" the peptide with an immunogenic peptide, one could construct a DNA which would result in such fusion product. The tag may be at the N-terminus or the C-terminus. An example is a "FLAG-tag" version of the peptide. This type of "tagging" is useful to bind the peptide using reagents, such as antibodies, which are selective for the tag. Such binding may be for detection of the location or amount of peptide, or for peptide capturing processes where, for example, an affinity column is used to bind the tag, and thus the desired peptide. Other types of detectable labels, such as radioisotopes, light-emitting (e.g., fluorescent or phosporescent compounds), enzymatically cleavable, detectable antibody (or modification thereof), or other substances may be used for such labeling of the peptide.

To enhance functional properties, the peptide may also be derivatized by the attachment of one or more other chemical moieties. Such chemical moieties may be selected from among various water soluble polymers. The polymer should be water soluble so that the peptide to which it is attached is miscible in an aqueous environment, such as a physiological environment. The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyamino acids (either homopolymers or random or non-random copolymers; see further below regarding fusion molecules), and dextran or poly(n-vinyl pyrolidone)polyethylene glycol, propylene glycol homopolymers, polypropylene oxide/ethylene oxide co-polymers, polyoxyethylated polyols, polystyrenemaleate and polyvinyl alcohol. Polyethylene glycol propionaldehyde may have advantages in manufacturing due to its stability in water.

Fusion peptides in accordance with the present invention may be prepared by attaching polyamino acids to the peptide of SEQ ID NO: 1. For example, the polyamino acid may be a carrier protein which serves to increase the circulation half life of the peptide. The polyamino acid should be one which does not create a neutralizing antigenic response, or other adverse in vivo response. The polyamino acid may be selected from the group consisting of serum album (such as human serum albumin), an antibody or portion thereof (such as an antibody constant region, sometimes called "$F_c$") or other polyamino acids. The location of attachment of the polyamino acid may be at the N-terminus of the peptide moiety, or other place, and also may be connected by a chemical "linker" moiety to the peptide.

The polymer may be of any molecular weight, and may be branched or unbranched. For polyethylene glycol, the preferred molecular weight is between about 2 kilodaltons (kDa) and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to peptide molecules will vary, as will their concentrations in the reaction mixture. In general, the optimum ratio (in terms of efficiency of reaction in that there is no excess unreacted peptide or polymer) will be determined by factors such as the desired degree of derivatization (e.g., mono, di-, tri-, etc.), the molecular weight of the polymer selected, whether the polymer is branched or unbranched, and the reaction conditions.

The chemical moieties should be attached to the peptide with consideration of effects on functional or antigenic domains of the peptide. There are a number of attachment methods available to those skilled in the art. See, for example, European Patent No. 0 401 384 (coupling PEG to G-CSF), and Malik et al., Experimental Hematology, Volume 20, pages 1028–1035 (1992) (reporting pegylation of GM-CSF using tresyl chloride). By way of illustration, polyethylene glycol may be covalently bound through amino acid residues via a reactive group, such as a free amino or carboxyl group. Reactive groups are those to which an activated polyethylene glycol molecule (or other chemical moiety) may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s) or other chemical moiety. Preferred for therapeutic manufacturing purposes is attachment at an amino group, such as at the N-terminus or to a lysine group. Attachment at residues important for receptor binding should be avoided if receptor binding is important.

One may specifically desire N-terminally chemically modified derivatives. Using polyethylene glycol as an illustration, one may select from a variety of polyethylene glycol molecules (by molecular weight, branching, etc.), the proportion of polyethylene glycol molecules to peptide molecules in the reaction mixture, the type of pegylation reaction to be performed, and the method of obtaining the selected N-terminally pegylated peptide. The method of obtaining the N-terminally pegylated preparation (i.e., separating this moiety from other monopegylated moieties if necessary) may be by purification of the N-terminally pegylated material from a population of pegylated peptide molecules. Selective N-terminal chemical modification may be accomplished by reductive alkylation which exploits the differential reactivity of different types of primary amino groups (lysine versus the N-terminal) available for derivatization in a particular protein. See PCT application WO 96/11953, published Aug. 25, 1996.

Any of the above mentioned derivatives may be used in the method of this invention.

The peptide of SEQ ID NO: 1 or a derivative thereof can be formulated into a composition suitable for administration by injection, or for oral, pulmonary, nasal, transdermal, or other forms of administration. Included within the invention are pharmaceutical compositions comprising effective amounts of the peptide or derivative product together with pharmaceutically acceptable diluents, preservatives, solubilizers, emulsifiers, adjuvants and/or carriers. By "effective amount" is meant an amount sufficient to produce a measurable biological (e.g., mitogenic) effect on the treated sensory epithelial cells or tissue. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc., or into liposomes. See, for example, PCT application WO 96/29989 (Collins et al.), published Oct. 3, 1996. Hyaluronic acid may also be used, and this may have the effect of promoting sustained duration in the circulation. Such compositions may influence the physical state, stability, rate of in vivo release, and rate of in vivo clearance of the present proteins and derivatives. See, for example, Remington's Pharmaceutical Sciences, 18th Edition, Mack Publishing Co., Easton, Pa., pages 1435–1712 (1990). The compositions may be prepared in liquid form, or may be in dried powder, such as lyophilized form. Implantable sustained release formulations are also contemplated, as are transdermal formulations.

The peptide may be chemically modified so that oral delivery of the derivative is enhanced. Generally, the chemical modification contemplated for the present purposes is the attachment of at least one moiety to the peptide itself, where this moiety permits (a) inhibition of proteolysis and (b) uptake into the blood stream from the stomach or intestine. Also desired is the increase in overall stability of the peptide and increase in circulation time in the body. See PCT application WO 95/21629, Habberfield, "Oral Delivery of Chemically Modified Proteins" (published Aug. 17, 1995), and U.S. Pat. No. 5,574,018 (Habberfield et al.), issued Nov. 12, 1996.

Nasal delivery of the peptide of SEQ ID NO: 1 (or derivative) is also contemplated. Nasal delivery allows the passage of the peptide (or derivative) to the blood stream directly after administering the therapeutic product to the nose, without the necessity for deposition of the product in the lung. Formulations for nasal delivery include those with absorption enhancing agents, such as dextran or cyclodextran.

If desired, the peptide or derivative may also be administered systemically in a sustained release formulation or preparation. Suitable examples of sustained release preparations include semipermeable polymer matrices in the form of shaped articles, for example, films or microcapsules. Sustained release matrices include polyesters, hydrogels, polylactides (U.S. Pat. No. 3,773,919), copolymers of L-glutamic acid and gamma ethyl-L-glutamine (Sidman et al, Biopolymers, Volume 22, pages 547–556, 1983), poly (2-hydroxyethyl-methacrylate) (Langer et al., Journal of Biomedical Materials Research, Volume 15, pages 167–277, 1981, and Langer, Chemical Technology, Volume 12, pages 98–105, 1982), ethylene vinyl acetate (Langer et al., above) or poly-D(−)-3-hydroxybutyric acid. Sustained-release compositions also may include liposomes, which can be prepared by any of several methods known in the art; see, for example, Epstein et al., Proceedings of the National Academy of Sciences USA, Volume 82, pages 3688–3692 (1985), and Hwang et al., National Academy of Sciences USA, Volume 77, pages 4030–4034 (1980).

Typically, the peptide will be in highly purified form, and the therapeutic composition will normally be presterilized for use, such as by filtration through sterile filtration membranes.

The amount of peptide that will be effective in vivo may vary. One skilled in the art will be able to ascertain effective dosages by administration and observing the resulting therapeutic effect. Preferably, the formulation of the peptide in a pharmaceutical composition will be such that between about 0.10 $\mu$g/kg/day and 10 mg/kg/day will yield the desired therapeutic effect. The composition may be administered as a single dose, or as two or more doses (which may or may not contain the same amount of peptide) over time, or on a continuous basis.

The invention is described in further detail with regard to the following working examples, which are not intended to be limiting.

EXAMPLE 1

Cell Proliferation in Primary Culture of Sensory Epithelium

Sensory epithelial cells obtained from utricles in the inner ear of both seven day-old (infant) rats and six week-old (adult) rats were isolated with the use of thermolysin treatment; see Corwin et al., Abstracts of the Association for Research in Otolaryngology, Volume 18, page 87 (1995). All edges were trimmed away and the central portion of the epithelium was cut into quarters. Epithelial cells from the infant rats were cultured in DMEM/F12 with 10% FBS (Gibco BRL, Grand Island, N.Y.), and 3 micrograms per milliliter ($\mu$g/ml) of mitosis tracer BrdU (Aldrich Chemicals, Milwaukee, Wis.) for seventy-two hours, with or without 50 nanograms per milliliter (ng/ml) of the peptide of SEQ ID NO: 1 or 50 ng/ml of recombinant derived FGF-10, recombinant derived FGF-16, recombinant derived ciliary-derived neurotrophic factor (CNTF), recombinant derived neurotrophic growth factor (NGF), recombinant derived glial-derived neurotrophic factor (GDNF), recombinant derived keratinocyte growth factor (KGF), or a control (no growth factor present). The experiment was ended by fixing in 4% paraformaldehyde for one hour.

For the adult rats, the total time for cell culture was thirteen days, with the peptide of SEQ ID NO: 1 or other growth factor being added for the last five days and the BrdU (3 $\mu$g/ml) for the last two days. The experiment was ended as above by fixing the explants in paraformaldehyde.

After several washes, the explants were immunostained for calretinin (a vestibular organ hair cell marker) using rabbit antiserum (SWant Swiss Antibodies, Belinzona, Switzerland), diluted 1:10,000. The secondary antibody was goat anti-rabbit immunoglobulin conjugated to biotin, diluted 1:1,000. Extensive washes were followed by incubating the explants with egg white avidin conjugated to Cy3, diluted 1:1,000. The explants were fixed again with paraformaldehyde as described above, then processed for BrdU immunostaining (a measure of cell proliferation) using standard immunostaining protocols. The mouse monoclonal ant-BrdU antibody was obtained from Caltag Laboratories of San Francisco, Calif. The secondary antibody, a goat anti-mouse conjugated to FITC, was obtained from Antibodies, Inc. of Davis, Calif.

In the test group using cultured epithelia from infant rats, the number of BrdU-positive nuclei per piece of epithelium was found to be significantly higher in the peptide-treated (SEQ ID NO: 1) group, 397±33, when compared to: the control (untreated) group (50±7), the FGF-10-treated group (11±4), the FGF-16-treated group (100±16), the CNTF-treated group (23±3), the NGF-treated group (50±9), the GDNF-treated group (37±13), and the KGF-treated group (89±16). See FIG. 2 for a graphical representation of these results.

The mitogenic activity of the peptide of SEQ ID NO: 1 was also compared with glial growth factor (GGF) using a similar protocol. This test was additionally used to evaluate whether the peptide of SEQ ID NO: 1 was active on sensory epithelium derived from adult (rather than just infant) rats. While treatment with the peptide of SEQ ID NO: 1 induced a 32.5-fold increase in proliferation of adult rat sensory epithelial cells over the control group, treatment with GGF only induced a 22.3-fold increase in the proliferation of such cells. See FIG. 3 for a graphical representation of these results.

Figure 4B:
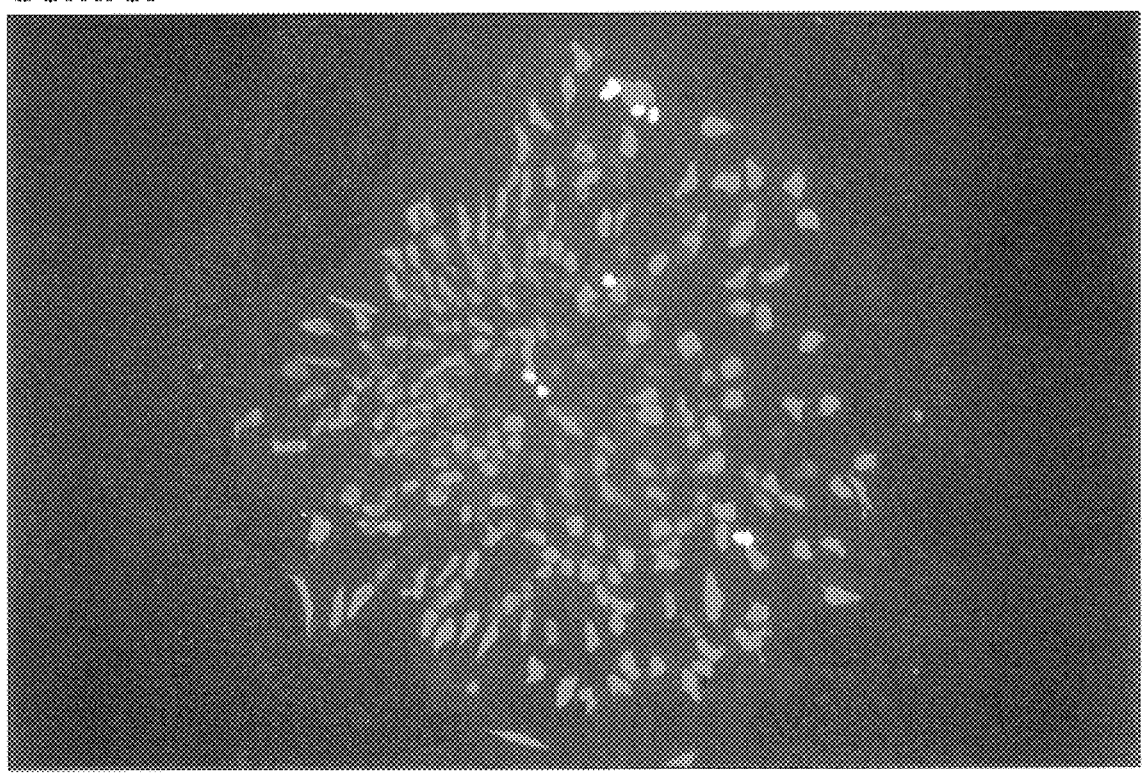

The effect of treatment with the peptide of SEQ ID NO: 1 in the primary cell culture of infant rat sensory epithelium is also shown very clearly in FIG. 4A and 4B. As can be seen, there is a very noticeable increase in the presence of BrdU-positive nuclei (shown as lighter colored dots) in the supporting cells which have been treated with the peptide of SEQ ID NO: 1 (FIG. 4A) versus the control (untreated) cells (FIG. 4B). Hair cells immunostained with calretinin are shown in the background as grayish spots. The proliferation of supporting cells is a necessary prerequisite for hair cell generation/regeneration in the vestibular and auditory organs. The effect observed here with the peptide of SEQ ID NO: 1 is very potent, and superior to any in vitro result reported in the literature so far for any other growth agent. Typically, cell culture conditions are not effective for generating new hair cells. The effect obtained here with supporting cells is very surprising and suggests that a positive effect will also be obtained in vivo which may lead to hair cell generation.

EXAMPLE 2
Comparison with Other NDF/heregulins

Using the test procedure of Example 1, the peptide of SEQ ID NO: 1 was compared with members of the NDF-heregulin family in primary cultures of young rat utricular sensory epithelial cells, at a treatment concentration of 50 ng/ml in each case. The comparison molecules were as follows: recombinant rat NDFα2 (see Wen et al., Molecular and Cellular Biology, above), recombinant human NDFα2, and recombinant human NDFβ1 (See PCT application WO 94/28133, published Dec. 8, 1994, for a description of these two proteins).

As can be seen from FIG. 5, the most potent effect was obtained with the peptide of SEQ ID NO: 1 ("Peptide"), which represented a 29-fold increase in induction of cell proliferation over the control.

EXAMPLE 3
Proliferation of Cells from Rodent Vestibular Organ

An established utricular cell line was derived from a transgenic mouse, using the procedure described by Gu et al. in Abstracts of the Association for Research in Otolaryngology, Volume 21, page 16 (1998). The cell line was cultured at 37° C. for three days in DMEM/F12 (Gibco BRL), containing N2 supplement (Sigma Chemical Company, St. Louis, Mo.) in a proportion of 1:100, under conditions restricting oncogene expression. For the treated group, fifty nanograms per milliliter of the peptide of SEQ ID NO: 1 were added twenty-four hours prior to fixation. Three micrograms per milliliter of BrdU (Aldrich Chemicals) were added for the final sixteen hours.

Cell proliferation was measured by ELISA for BrdU. Briefly, cells were fixed with 4% paraformaldehyde (Amersham, Life Sciences, Cleveland, Ohio) for one hour at room temperature. After treatment with 2N HCl for twenty minutes, the cells were washed and then sequentially incubated for one hour with a monoclonal antibody against BrdU (Caltag Laboratories) and horse anti-mouse antibody conjugated to biotin (Vector Laboratories, Burlingame, Calif.). After washing, the cells were further incubated with Europium streptavidin (Wallac Inc., Gaithersburg, Md.) diluted 1:1,000 and processed for time-resolved fluorescence in accordance with the manufacturer's recommendations. The signal was read on a Victor 1420 multi-label counter (Wallac Inc.).

The ELISA reading from the peptide-treated group (SEQ ID NO: 1) was found to be 1.7 times higher than for the control (untreated) group. These results, taken together with those of Example 1, above, demonstrate that the peptide of SEQ ID NO: 1 is a potent stimulator of cells of the vestibular epithelium from both newborn and mature rodents.

EXAMPLE 4
Generation of Monoclonal Antibodies Against Sensory Epithelial Cells of Rodent Inner Ear The lack of a specific marker for sensory epithelium cells adds to the challenges associated with research on hair cell regeneration in the inner ear of mammals. Monoclonal antibodies against hair cells have been reported in the literature; Finley et al., Assoc. Res. Otolaryngol. Abstr., Volume 20, page 16 (1997) and Holley et al., J. Neurocytol., Volume 24, pages 853–864 (1997). However, none of these antibodies are specific to supporting cells in the mammalian vestibular organs.

The following is a description of the preparation of four distinct monoclonal antibodies raised against rat utricular epithelia which specifically label supporting cells of the vestibular organs in the inner ear of the rodent. These antibodies constitute an additional aspect of the present invention.

In this method, sensory epithelia were isolated from adult rat inner ear utricles by the thermolysin method; see above for description. Seventy pieces of epithelia were homogenized by ultrasound, and then emulsified with Freund's adjuvant (Sigma Chemical Company, St. Louis, Mo.). The emulsification product was injected intraperitoneallly into Balb/c mice on days 0, 29 and 53, prior to fusion of day 56. The fusion time was determined when the serum derived from bled mice showed high titer against the antigen (i.e., the utricle extract). Mouse splenocytes were harvested and then fused with HL-1 myeloma cells (Kohler and Milstein, Nature, Volume 256, pages 495–497 (1975). Screening for monoclonal antibodies was conducted by immunostaining on frozen 10-micron sections of rat utricle.

Briefly, adult rat utricles were rapidly isolated and fixed with 4% paraformaldehyde for one hour. The tissues were transferred sequentially to 5%, 10%, 15% and 20% sucrose solutions in a phosphate buffer for twenty four hours each. The tissue was then embedded in 7.5% gelatine in the 20% sucroise solution for one hour at 37° C. The tissues were then mounted in a cryomold (Polysciences, Inc. Warrington, Pa.) and frozen at −30° C., and 10-micron sections were generated on six-well chamber slides (Roboz Instruments, Inc., Rockville, Md.) and immunostained using the manufacturer's recommended procedure. Over thirty hybridomas were chosen for selective staining of sensory epithelium. Double staining with calretinin and monoclonal antibodies on both cultured utricular epithelium and frozen rat utricle sections resulted in the selection of four monoclonal antibodies (labeled "SC-1", "SC-2", "SC-3" and "SC-4", respectively).

Each of the monoclonal antibodies specifically stained the supporting cells, but with a characteristically different pattern. SC-1 stained the top portion of the supporting cells brightly, while gradually decreasing around the cell nuclei. SC-2 stained only the top portion of the supporting cells. SC-3 immunoreactivity was concentrated on the lower cytoplasmic portion of the supporting cells in neotal rat utricles, and migrated to the upper portion in adult utricles. SC-4 immunoreactivity was found mostly in the supporting cell apex of the adult utricle. SC-4 and SC-3 immunostaining was found in embryonic progenitors of supporting cells of the inner ear.

A monoclonal antibody (SC-4) prepared as described above was deposited with the American Type Culture Collection (ATTC), 10801 University Boulevard, Manassas, Va. 20110, on Nov. 18, 1998, under accession number HB-12598.

The invention described above is defined in the appended claims.

---

---

What is claimed is:

1. The monoclonal antibody which has been deposited with the American Type Culture Collection under accession number HB-12598.

* * * * *

SEQUENCE LISTING

```
<160> NUMBER OF SEQ ID NOS: 2

<210> SEQ ID NO 1
<211> LENGTH: 52
<212> TYPE: PRT
<213> ORGANISM: Human

<400> SEQUENCE: 1

Ser His Leu Val Lys Cys Ala Glu Lys Glu Lys Thr Phe Cys Val Asn
  1               5                  10                  15

Gly Gly Glu Cys Phe Met Val Lys Asp Leu Ser Asn Pro Ser Arg Tyr
             20                  25                  30

Leu Cys Lys Cys Gln Pro Gly Phe Thr Gly Ala Arg Cys Gln Asn Tyr
         35                  40                  45

Val Met Ala Ser
     50

<210> SEQ ID NO 2
<211> LENGTH: 156
<212> TYPE: DNA
<213> ORGANISM: Human

<400> SEQUENCE: 2
agccatcttg taaaatgtgc ggagaaggag aaaactttct gtgtgaatgg aggggagtgc      60
ttcatggtga aagacctttc aaacccctcg agatacttgt gcaagtgcca acctggattc     120
actggagcaa gatgtcaaaa ctacgtaatg gccagc                              156
```